United States Patent
Yang et al.

(10) Patent No.: US 11,761,017 B2
(45) Date of Patent: Sep. 19, 2023

(54) RICE THERMO-SENSITIVE MALE STERILE GENE MUTANT TMS18 AND USES THEREOF

(71) Applicant: Shanghai Normal University, Shanghai (CN)

(72) Inventors: Zhongnan Yang, Shanghai (CN); Jun Zhu, Shanghai (CN); Yueling Li, Shanghai (CN); Yanfei Zhang, Shanghai (CN)

(73) Assignee: SHANGHAI NORMAL UNIVERSITY, Shanghai (CN)

( * ) Notice: Subject to any disclaimer, the term of this patent is extended or adjusted under 35 U.S.C. 154(b) by 0 days.

(21) Appl. No.: 17/499,864

(22) Filed: Oct. 13, 2021

(65) Prior Publication Data

US 2022/0119836 A1 Apr. 21, 2022

(30) Foreign Application Priority Data

Oct. 16, 2020 (CN) .......................... 202011109557.0

(51) Int. Cl.
*A01H 1/02* (2006.01)
*C12N 9/04* (2006.01)
*C12N 15/82* (2006.01)

(52) U.S. Cl.
CPC ......... *C12N 15/8289* (2013.01); *A01H 1/023* (2021.01); *C12N 9/0006* (2013.01)

(58) Field of Classification Search
None
See application file for complete search history.

(56) References Cited

U.S. PATENT DOCUMENTS 10,619,168 B2 * 4/2020 Tang ...................... C12N 15/00
2015/0353958 A1 12/2015 Tang et al.

OTHER PUBLICATIONS

Chang, Z et al, Construction of a male sterility system for hybrid rice breeding and seed production using a nuclear male sterility gene, 2016, PNAS, 113, 14145-14150 (Year: 2016).*
Oryza sativa GB Accession No. KX066198.1, 2016 (Year: 2016).*
Barman, NB et al, Generation of a new thermo-sensitive genic male sterile rice line by targeted mutagenesis of TMS5 gene through CRISPR/Cas9 system, 2019, BMC Plant Biology 19:109 (Year: 2019).*
Browne, RG et al. Anther Morphological Development and Stage Determination in Triticum aestivum, 2018, Frontiers in Plant Science, 9:228. (Year: 2018).*
Fan, Y and Zhang Q, Genetic and molecular characterization of photoperiod and thermo-sensitive male sterility in rice, 2018, Plant Reproduction 31: 33-14. (Year: 2018).*
Wu et al, Characteristics of Fertility Transition Response to the Cumulative Effective Low Temperature in a Two-Line Male Sterile Rice Cultivar, 2021, Rice: 14:71 (Year: 2021).*
NCBI GenBank KX066198 2016 (Year: 2016).*
Chen et al., Transcriptomics Analysis on Fertility Conversion in Thermosensitive Genetic Male Sterility Line Zhu1S under High Temperature, 2022, Agronomy 12:1255 (Year: 2022).*
Zhou H et al, Development of Commercial Thermo-sensitive Genic Male Sterile Rice Accelerates Hybrid Rice Breeding Using the CRISPR/Cas9-neudated TMS5 Editing system, 2016, Scientific Reports 6:37395. (Year: 2016).*
Mamun EA et al, Effects of chilling on male gametophyte development in rice, 2006, Cell Biology International 30:583-591 (Year: 2006).*
Xu, J et al. Fine mapping and candidate gene analysis of ptgms2-1, the photoperiod-thermo-sensitive genic male sterile gene in rice (*Oryza sativa* L.), 2011, Theoretical and Applied Genetics 122: 365-372. (Year: 2011).*
Hamilton, S. How many rice varieties are there? 2006, International Rice Research Institute, https://ricetoday.irri.org/how-many-rice-varieties-are-there/ (Year: 2006).*

* cited by examiner

*Primary Examiner* — Anne Kubelik
*Assistant Examiner* — Aleksandar Radosavljevic (57) ABSTRACT

The invention discloses a rice temperature sensitive male sterile gene mutant tms18 and its uses. During the study of TMS18 gene, the inventors found that the changing of fertility was related to the structural integrity of the second layer of pollen outer wall. The inventors accidentally found the thermo sensitive male sterile mutant tms18. The fertility of the mutant was affected by different temperatures and can be restored under low temperature treatment. More importantly, the fertility sensitive period of the mutant was different from that of other thermo sensitive male sterile genes. This unique feature of the gene can provide a new theoretical basis and apply value for two-line hybrid rice breeding.

2 Claims, 5 Drawing Sheets

Specification includes a Sequence Listing.

RICE THERMO-SENSITIVE MALE STERILE GENE MUTANT TMS18 AND USES THEREOF

SEQUENCE LISTING

This application contains a Sequence Listing in form of ASCII text filed via EFS-Web and hereby incorporated by reference into the specification in its entirety. The name of the text file containing the Sequence Listing is 3-2021PC013US-SequenceListing-20230615. The size of the text file is 3100 kilobytes, and the text file was created on May 29, 2023.

CROSS-REFERENCE TO RELATED APPLICATION

This application claims all benefits under 35 U.S.C. § 119 from China Patent Application No. CN202011109557.0, filed on Oct. 16, 2020 in the China National Intellectual Property Administration, the content of which is hereby incorporated by reference.

TECHNICAL FIELD

The invention relates to the field of agriculture, in particular to a rice tempo-sensitive male sterile mutant and uses thereof, which can restore fertility under specific conditions.

BACKGROUND

Rice is a monocotyledonous annual herb and one of the most important food crops in the world. The heterosis is more obvious by using the Heterosis among varieties, subspecies and even distant heterosis. Rice male sterile materials are of great value in hybrid breeding and agricultural production.

After the use of photo-thermo-sensitive male sterile lines, hybrid rice produces three-line hybrid rice based on cytoplasmic male sterility and two-line hybrid rice dependent on photoperiod- and thermo-sensitive genic male sterility, P/TGMS. Three-line hybrid rice needs cytoplasmic male sterile line, restorer line and maintainer line, while two-line method includes photoperiod- and thermo-sensitive genic male sterile line and restorer line. Photoperiod- and thermo-sensitive genic male sterile line can reproduce itself under different environmental factors and can also be used for hybrid seeds production.

Therefore, in-depth analysis and mining of existing Photoperiod- and thermo-sensitive genes is more conducive to the application of molecular breeding. At present, there are about 20 genic male sterile lines positioned based on their response to light and temperature, but only 3 genes have been cloned. Although a certain degree of breakthrough has been made, further in-depth research is needed. There are relatively few resources of photoperiod- and thermo-sensitive genes, so it is necessary to explore new photoperiod- and thermo-sensitive gene resources.

SUMMARY OF THE INVENTION

During the study of gene TMS18, the inventor of the present application found that the change of its fertility is related to the structural integrity of the second layer of pollen outer wall. In the research process, the inventors accidentally obtained a thermo sensitive genic male sterile mutant tms18 of gene TMS18. The fertility of the mutant is affected by different temperatures and can be restored under specific circumstances. More importantly, the mutation sites of the mutant are different from other reported photo and thermo sensitive mutation sites, and the fertility sensitive period is also different from other thermo sensitive male sterile genes. At present, it is known that the sensitive period of fertility of cloned photo and thermo sensitive genic male sterile lines is mainly before pollen mother cell meiosis. However, the sensitive period of newly found thermo sensitive genic male sterile mutant tms18 is affected after pollen mother cell meiosis. This unique feature of the gene can provide a new theoretical basis and application value for two-line hybrid breeding. Moreover, due to the special and later time of low-temperature fertility recovery of tms18, it is more convenient to judge the fertility recovery period of corresponding plants, and then apply it in breeding. For example, the corresponding plants can be treated at low temperature after pollen mother cell meiosis to recovery its fertility.

The invention provides a rice thermo-sensitive male sterile gene mutant tms18 of SEQ ID No.1.

In addition, the invention also provides an expression vector containing the rice temperature sensitive male sterile gene mutant tms18.

The invention also provides a transgenic seed for a crop plant, wherein the genome of said transgenic seed comprises the rice thermo-sensitive male sterile gene mutant tms18 of SEQ ID No.1. Preferably, double strands of the chromosome of the seed both comprise the gene mutant tms18.

The invention also provides a method for cultivating transgenic rice, wherein the method includes introducing a rice temperature sensitive male sterile gene mutant tms18 of SEQ ID No.1 into rice seed cells, using the rice seed cells to cultivate rice seeds, and planting the rice seeds to obtain the rice.

Preferably, the method is used to cultivate fertility recoverable rice, the fertility of which can be recovered by low temperature treatment.

Preferably, the temperature for low temperature treatment is lower than 23° C.

Preferably, the low temperature treatment is performed on the rice after their pollen mother cell meiosis.

Preferably, the method is used to cultivate Recessive Male Sterile transgenic plants.

The invention also provides a use of the rice thermo-sensitive male sterile gene mutant tms18 of SEQ ID No.1, wherein the rice thermo sensitive male sterile gene mutant tms18 is used to regulate the thermo sensitive fertility traits of plants, or is used as a selection marker of transgenic plants by making use of its reversible temperature sensitive fertility feature.

The rice temperature sensitive male sterile gene mutant tms18 can provide rice with a reversible temperature sensitive fertility character. More specifically, the character is that the rice containing the mutant tms18 shows fertility recovery under the condition of low temperature (such as 27-25, preferably 25-23° C.); while under high temperature (e.g. 28-29, preferably 29-32° C.), the rice show sterile characters.

The thermo-sensitive sterile mutant gene of the invention is sensitive to temperature. When it is treated at low temperature, it can achieve more than 90% fertility recovery effect. Moreover, the low temperature response time of the gene mutant has particularity. Its response time is at the 9th-10th stage of pollen development, when the appearance characteristics of pollen are more obvious, easier to judge, and more conducive to the accurate control by experiment. Therefore, during the process of making use of this gene mutant tms18, the corresponding plants can be treated at low temperature during this period.

DESCRIPTION OF FIGURES

FIG. 5 shows the SEM observation results of anthers and pollen of wild-type and tms18 mutants at different temperatures, wherein F and K portions show the SEM observation results of anthers of wild-type and containing tms18 materials at high temperature and low temperature respectively; B, G and L portions show the scanning electron microscope observation results of anther amplification structure of wild-type and tms18 materials at high temperature and low temperature, respectively; C, H and M portions show the SEM observation results of the structure of wild-type and tms18 materials after anther cracking at high temperature and low temperature, respectively; D, I and N portions show the SEM observation results of mature pollen of wild-type and tms18-material at high temperature and low temperature, respectively; E, J and O portions show the SEM observation results of mature pollen amplification structure of wild-type and tms18 materials at high temperature and low temperature, respectively; HT stands for high temperature treatment (>28° C.); LT stands for low temperature treatment (<23° C.); A. The scales in F and K are 200 μm, in B, G, L, D, I and N are 10 μm, and in C, H, M, E, J and O are 1 μM.

FIG. 6 shows the TEM observation results of wild-type and tms18 mutant pollen at different temperatures; wherein A-E portions show the pollen transmission electron microscope observation results of wild-type Anthers from stage 7 to stage 10 and stage 12; F-J portions show the pollen transmission electron microscope observation results of tms18 mutant anther from stage 7 to stage 10 and stage 12 under high temperature; K-0 portions show the result of TEM observation of pollen in the $7^{th}$ to $10^{th}$ and $12^{th}$ anthers of tms18 mutant under low temperature; the small figure on the right of each figure is the enlarged result of the figure. HT stands for high temperature treatment (>28° C.); LT stands for low temperature treatment (<23° C.). AP represents abnormal pollen; Ba represents rod structure; E represents anther epidermis; EN represents anther endothelium; Ex stands for pollen wall; Msp stands for microspore; Ne represents the inner layer of the outer wall; PE represents the primary outer wall; Se represents the outer layer of the outer wall; T stands for felt layer; TDS stands for tetrad.

EMBODIMENTS

The invention is described in detail below in combination with the accompanying drawings and their embodiments, but the protection scope of the invention is not limited to the scope described in the embodiments.

The inventors took the *Oryza sativa* ssp. *japonica*, ZH11 as the material, screened with ethyl methanesulfonate (EMS) to obtain the plant material of thermo-sensitive genic male sterile line TMS18, and obtained the thermo-sensitive male sterile mutant tms18 in the experiment. The gene sequence of the mutant is shown in SEQ ID No.1 (including exons and introns), and the edited amino acid sequence is shown in FIG. 12. The specific experimental process is described in detail below.

Plant Materials and their Planting Process

In this embodiment, the rice material used is the *japonica* rice variety ZH11. Referring to Zhang et al. 2007 (Zhang Z B, Zhu J, Gao J F, et al. Transcription factor AtMYB103 is required for anther development by regulating tapetum development, callose dissolution and exine formation in *Arabidopsis*. Plant Journal, 2007, 52: 528-538), EMS mutants are induced and screened. During the screening, the mutant plants containing the thermo-sensitive male sterile mutant tms18 of SEQ ID No.1 was accidentally obtained.

The inventors, using the recessive homozygous male sterile plant containing the mutant tms18 as the female parent (ovule donor) and using the target rice variety as the male parent (pollen donor), hybridized these two kinds of rice at high temperature, and obtained F1 seeds. Then, the inventors cultivated the F1 seeds to obtain the F1 plants. The F1 plants were self pollinated to obtain the F2 seeds. In the F2 plants, those plants with tms18 recessive homozygous sites were screened.

Figure 2:
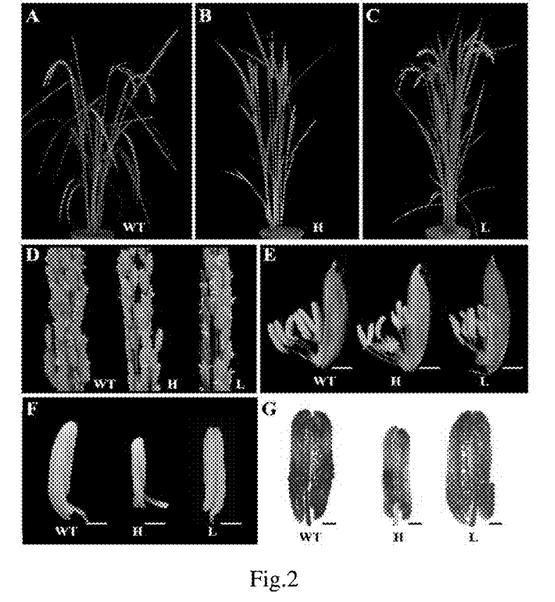
FIG. 2 shows the phenotypic analysis results of wild-type and temperature sensitive plants containing tms18 at different temperatures, in which A-C portions show the phenotypic of wild-type and tms18 mutant plants after heading; D portion shows anthers of wild type and tms18 mutant plants after flowering; E portion shows anthers of wild type and osacos12 mutant plants after spikelet shelling; H portion shows single anther of wild type and osacos12 mutant; F portion shows Alexander dye solution of wild type and osacos12 mutant anthers; the character "H" stands for high temperature treatment (>28° C.); the character "L" stands for low temperature treatment (<23° C.); The scale length (E-F) is 100 μm; (G) 200 μM.

Identification of temperature sensitive characteristics of tms18 In this example, from May 18, 2018, 24 copies of three kinds of rice are cultivated per week, that is, rice of ZH11 wild type, rice of Annong S-1 male sterile line and rice containing mutant tms18, and obtaining corresponding seedlings. After the seedlings have already been cultivated and reach a certain height, the seedlings were inserted into Fengxian field in Shanghai (a place of China) for planting. From July 26 to August 1, the average temperature in Shanghai reached the highest point, about 30.5° C., and the first batch (germinated on May 18) reached booting stage (pollen development stage). Since the tms18 plants were treated by high temperature, after the tms18 plant materials flowering and selfing, they showed almost complete sterility because there were no pollen (as shown in FIG. 2). In the eighth batch of materials (plants) (Germinating on July 6), since the booting time was about September 10, the average temperature in Shanghai fell to 26.5 degrees, the pollen development partially returned to normal due to low temperature, and the fertility of self bred materials of the plants were partially restored. It is verified that the high temperature sterility of tms18 plant is better than that of Annong S-1 (the name of another kind of rice).

Cytological Analysis

The anther slices at different development (growth) stages of rice were photographed with Olympus dx51 digital camera. The fresh stamens and pollen grains were wrapped with 8 nm gold particles for scanning by electron microscopy, and observed by JSM-840 microscope. For the transmission electron microscope experiment, the rice spikelets were fixed on ice in the fixed solution (0.1M phosphate buffer containing 2.5% glutaraldehyde, pH 7.2). Spikelet materials are further embedded in resin ('hard plus' embedding resin, Unite Kingdom). Ultrathin sections (50-70 nm) were observed by jem-1230 transmission electron microscope (jeol, Japan).

RNA Extraction and Quantitative RT-PCR

RNA was extracted from spikelet tissue of mature soil cultured rice plants by Trizol reagent (Invitrogen, USA). Using poly DT (12-18) primers; using MMLV reverse transcriptase and corresponding reagents reverse transcribe RNA and obtain the first cDNA strand (60 minutes, 42° C.). The synthesized cDNA strand was used as a template for PCR. SYBR Green I master mix (Toyobo, Japan) was used for quantitative RT-PCR detection through ABI prism 7300 system (Applied Biosystems, USA). The program parameters of quantitative RT-PCR were: 95° C. for 5 minutes, 94° C. for 10 seconds, denaturation for 40 cycles, annealing at 60° C. for 1 minute. β-Actin was used as control.

It should be noted that the plant materials in the invention are cultured in fertile soil. The high temperature and low temperature treatment are performed in glass greenhouse and artificial intelligence lighting room. The high-temperature treatment temperature is generally in summer or in the environment with an average temperature higher than 28° C. the low-temperature treatment is generally in autumn or under the condition of an average temperature of 22-24.5° C.

Figure 1:
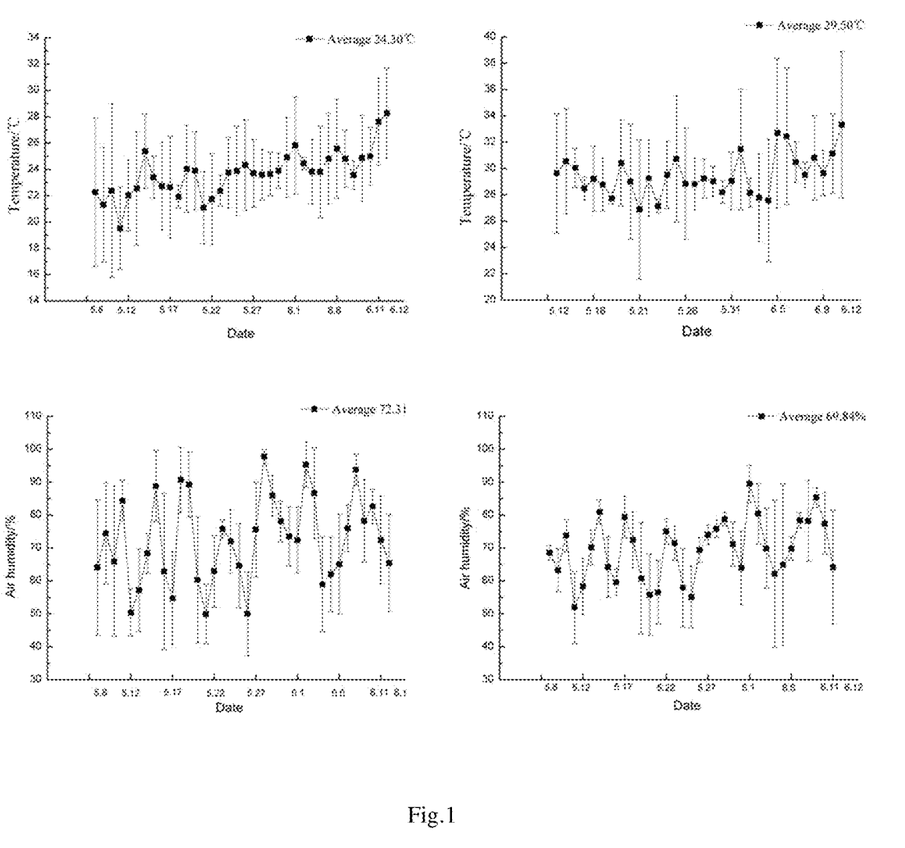
FIG. 1 shows the environmental temperature and humidity during fertility changes of plants containing tms18.

As shown in the figures, as compared with the wild type, the nutrition and development of tms18 mutant was normal without significant difference (FIG. 2A-C). Tms18 plants showed male sterility under high temperature (>28° C.) (FIG. 1), and the fertility of tms18 plants could be restored under low temperature (<23° C.) (FIG. 1). After flowering, the anthers of tms18 mutant plants did not disperse pollen at high temperature, but the pollen in the anthers of tms18 mutant plants was normal at low temperature (FIG. 2D). Through the observation of spikelets of wild-type and tms18 mutant plants, it was found that there were no significant difference in lemma and palea, but the anthers of wild-type plant were plump and yellow, while the anthers of tms18 mutant plants obviously shrunk and became smaller at high temperature and returned to plump state at low temperature (FIG. 2 E-F). Alexander staining results of anthers showed that wild-type pollen accumulated rich contents and showed purplish red, while no pollen grains stained purplish red could be seen in the tms18 mutant at high temperature, but returned to normal at low temperature, indicating that the anther development of tms18 mutant was affected by temperature, and low temperature could make up for the development defect of male gametophyte in tms18 mutant.

Figure 3:
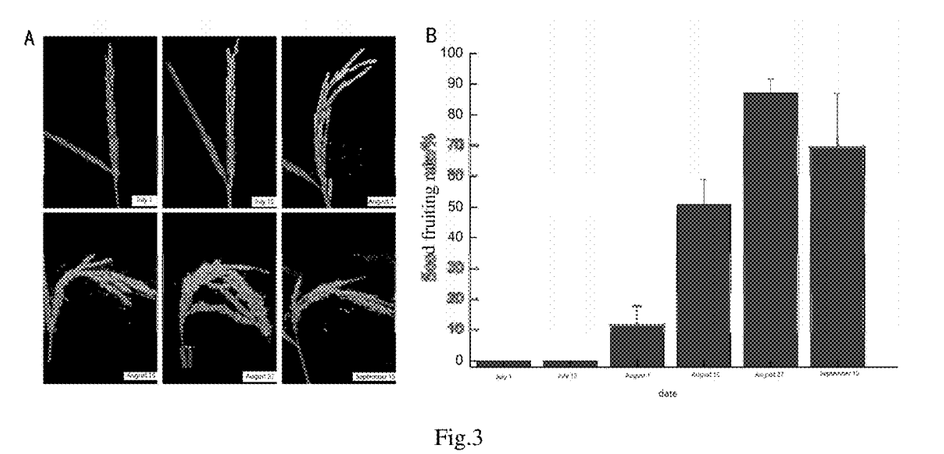
FIG. 3 shows the results of seed setting rate of plants containing tms18 under treatments at different time, wherein A portion shows seed setting phenotypes of tms18 mutant after heading; B portion shows the statistical table of seed setting rate of tms18 mutant after heading.

In order to verify the response to different temperatures of tms18, the inventors planted the tms18 mutant at different periods of time. The planting time is from July 1 to September 15. Germination planting is carried out every two weeks to observe the fertility recovery. As shown in FIG. 3, all tms18 materials transplanted before the middle of July showed complete sterility phenotype, and some fertility of the materials transplanted at the beginning of August recovered, with a recovery rate of about 10%. With the postponement of transplanting time, the fertility of tms18 material under natural low temperature can be basically similar to that of wild-type material, the spikelet drooping is obvious, and the seed setting rate is about 90%. The results showed that tms18 had better fertility recovery under appropriate temperature.

Mechanism Analysis:

The Inventors Found that Low Temperature can Make Up the Development Defects after release from tetrads of the tms18 mutant (similar expressions in this application refer to the rice plant/material containing the tms18 gene. The tms18 mutant plant cultivated by the inventor is obtained through experiments. Those skilled in the art can introduce the tms18 gene mutant into the rice plant by using existing *Agrobacterium* introducing methods according to the gene sequence provided by the invention).

Figure 4:
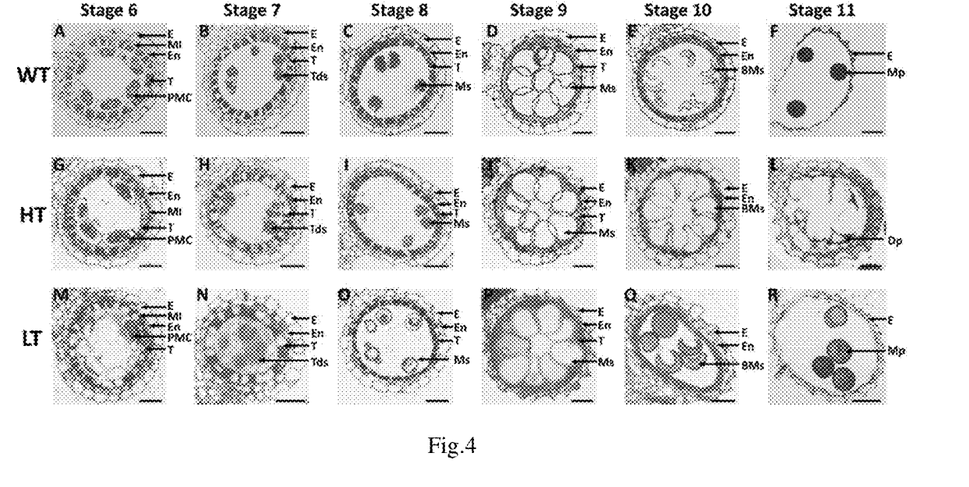
FIG. 4 shows the cytological observation results of anther development of wild-type and tms18 mutants at different temperatures.

In order to analyze the changes and differences of anther and pollen development of plants containing tms18 at different temperatures, the young spikelets and florets of wild-type ZH11 and tms18 mutants with anther length of 1-5.6 mm were observed by semi-thin sections. The results of semi-thin sections of wild-type and tms18 mutant plants under high temperature showed that from stage 6 to 8, the development of anthers could normally undergo meiosis and form tetrads, and there was no significant difference between the two kinds of plants (FIGS. 4 a-c and G-I). The wild-type tapetum cells formed in the early stage and began normal PCD in the 9th stage. The microspore further developed and expanded. The sporopollen deposition on the pollen wall was relatively dense, and the pollen development was normal (FIG. 4D). In the 10th stage, microspores of wild-type development normally and concentrated to form crescent structure, tapetum cells continued to degrade, then developed into mature pollen, and finally formed plump and normal pollen grains (FIG. 4 E-F). Under high temperature, the tapetum of tms18 mutant basically did not change significantly in the early stage, but the development of pollen was abnormal in the later mature stage, and finally showed rupture and could not form normal pollen grains (FIG. 4, K-L). Under low temperature, the development of pollen and tapetum cells of tms18 mutant were normal, and normal pollen could be formed (FIG. 4 M-R).

Figure 5:
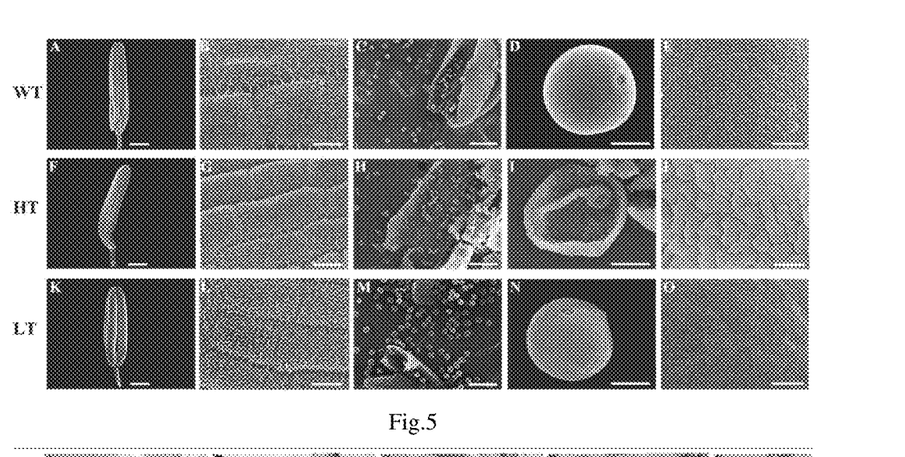

In order to better know the development of anther and pollen of tms18 mutant, the inventor observed the outer surface and inner surface of anther and the surface structure of pollen by scanning electron microscope. Under the scanning electron microscope, the wild-type anthers development normally and showed plump type, while the anthers of tms18 mutant were relatively small and shriveled compared with the wild-type at high temperature, and returned to normal at low temperature (FIGS. 5a, F and K). At the later stage of anther development, reticular waxy and horny structures appeared on the normal development surface of the wild type. There was no significant difference in the anther surface of the tms18 mutant at low and high temperature (FIGS. 5b, G and L). Through the observation of the structure of anther inner wall, it found that there were more dense globular structures in the anther inner wall of wild-type and tms18 mutant no matter at high or low temperature (FIGS. 5C, h and m), but the pollen in the anther of tms18 mutant showed a shrinkage phenotype at high temperature. In addition, compared with the dense structure of wild-type pollen outer wall, the structure of tms18 mutant pollen outer wall has defects indicating cracking and obvious shrinkage (FIGS. 5, D-E, I-J, and N-O). This indicates that tms18 gene mutation does not affect the outer epidermis and inner surface of anthers, but will lead to the defective phenotype of pollen outer wall.

Figure 6:
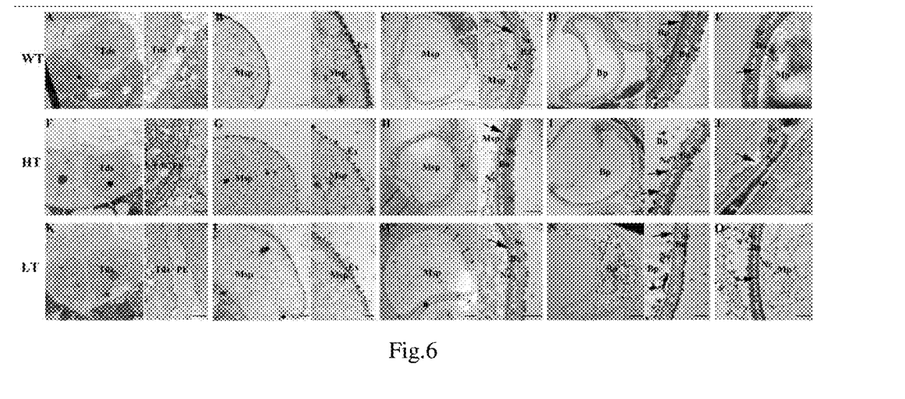
Figure 7:
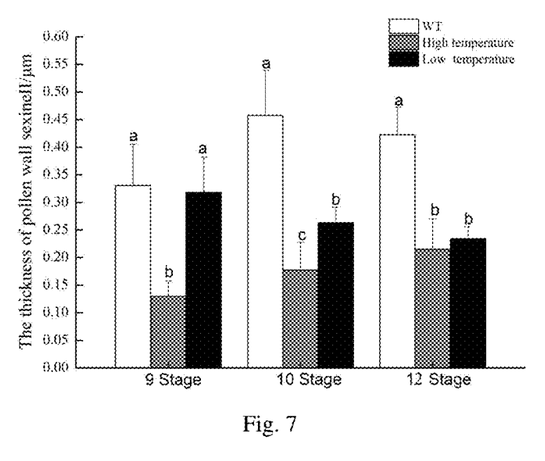
FIG. 7 shows the thickness of pollen outer wall II of wild type and tms18 mutant at different temperatures. In the figure, the thickness of pollen outer wall II of wild type and tms18 mutant at different temperatures at stages 9, 10 and 12, respectively. The data in the figure are the mean±standard deviation, and each group of data is 4 biological replicates. P<0.05.

In order to further make sure the condition of pollen outer wall of tms18 mutant at high and low temperature, the inventors observed the microspores of anther stages 7-10 and 12 by transmission electron microscope. The results showed that at the 7th stage of Anther Development (tetrad stage), the microspores of tms18 mutant and wild-type were surrounded by callose at different temperatures, and there were no significant difference there between (FIGS. 6a, F and K). Then microspores were released from callose and entered the 8th stage. According to the observation of pollen outer wall structure in this stage, it was found that sporopollen deposition gradually appeared on the pollen outer wall of wild-type pollen which was relatively dense, while the pollen outer wall sporopollen deposition of tms18 mutant was less at high temperature, while the pollen outer wall sporopollen deposition recovered at low temperature (FIGS. 6B, G and L). In phase 9, the wild-type microspore expanded and enlarged, and the structure of the pollen outer wall basically formed, showing a shape similar to character "エ". The microspore pollen outer wall of tms18 mutant can also show an "エ" shape structure under high temperature treatment, but its internal second layer structure became significantly thinner, and there were some obvious fractures inside (FIGS. 6C, H and M). In the 10th stage, the microspore entered the crescent structure. At high temperature, the defective structure of the second layer of the pollen outer wall can still be observed, while at low temperature, its thickness still did not recover, but its crack disappeared (see FIGS. 6, D, I and N). In the late stage of anther development (growth), the wild type can normally form fertile pollen, while the tms18 mutant has defects in the structure of pollen outer wall at high temperature, and finally can not form pollen normally, but can form mature pollen grains at low temperature. It shows that the temperature sensitivity of tms18 mutant is related to the structural defect of the second layer of pollen outer wall (FIG. 6, e, J and o). The second layer structure of pollen outer wall in the 9th, 10th and 12th stages of pollen development was statistically analyzed by Image J software. In the 9th-10th stage of pollen development, microspores entered the rapid expansion stage and concentration stage. Under high temperature treatment, the thickness of the second layer of pollen outer wall of tms18 mutant was significantly thinner, which was significantly reduced by 60.7% and 61.2% compared with the wild type, respectively. At the 10th stage of pollen development, the microspore entered the crescent structure. The tms18 mutant showed significant difference under high temperature and low temperature, microspore high temperature was 32.7% lower than that under low temperature. When the pollen development is in the mature stage, the pollen under high temperature treatment is still broken, while the normal pollen can be formed under low temperature treatment, but there is no significant difference in the thickness between the two. The above results show that temperature has a great influence on the pollen development of tms18 mutant, mainly in the 9th stage (microspore expansion stage) and the 10th stage (crescent stage), and after the meiosis stage of microspore mother cell. The genes with this characteristic have not been reported yet.

Tms18 Gene Encodes Glucose Methanol Choline (GMC) Family Oxidoreductases

Figure 8:
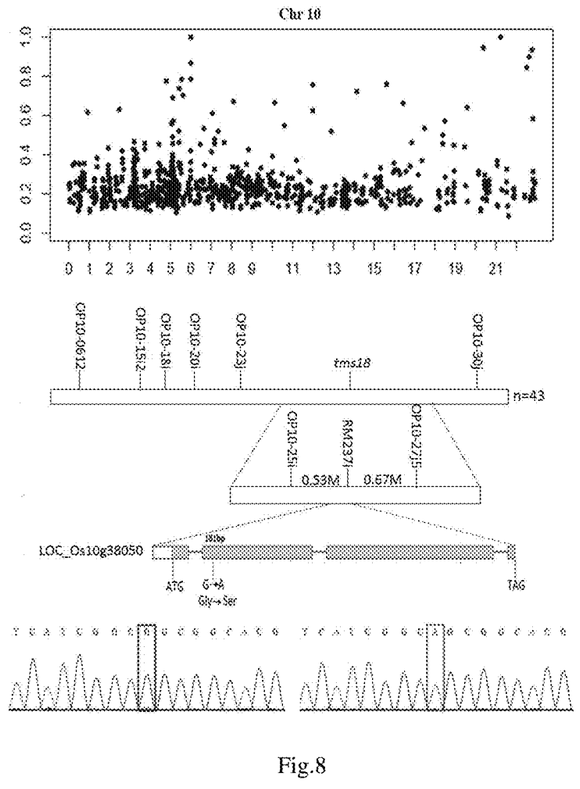
FIG. 8 shows sequence analysis results of tms18 gene, the sequencing and location analysis of tms18 gene SNP.
Figure 9:
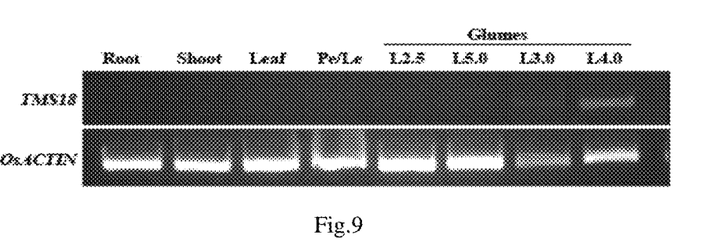
FIG. 9 shows the semi-quantitative PCR analysis results of tms18 gene in different tissues of rice, showing the semi quantitative analysis of tms18 gene and internal reference gene OsACTIN in different tissues. Le represents lemma; PA represents palea; L2.5 represents glume length is 2.5 mm; L3.0 represents glume length is 3.0 mm; L4.0 represents glume length is 4.0 mm; and L5.0 represents glume length is 5.0 mm.
Figure 10:
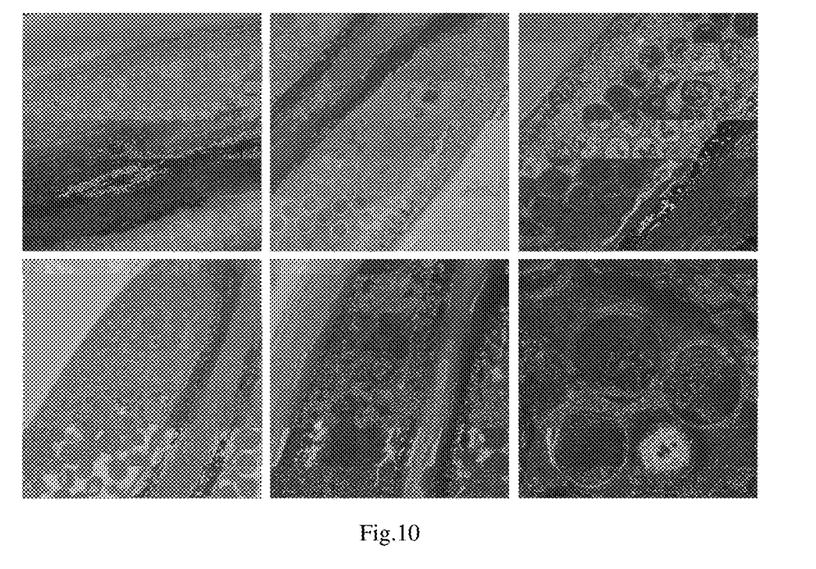
FIG. 10 shows the localization analysis results of tms18-gfp fluorescent protein in rice anthers.

Based on the whole genome SNP sequencing, the inventors found that there is a base mutation from G to A on 181 bp of the second exon of tms18 gene, which leads to the mutation of glycine encoded by wild-type Zhonghua 11 into serine (FIG. 8).

The inventor further carried out verification analysis by using genetic complementarity experiment.

The target gene fragments, including upstream promoter region and downstream region, were cloned and transformed into rice seeds including tms18, which are Hybrid, to carry out the cultivation of transgenic plants.

Figure 11:
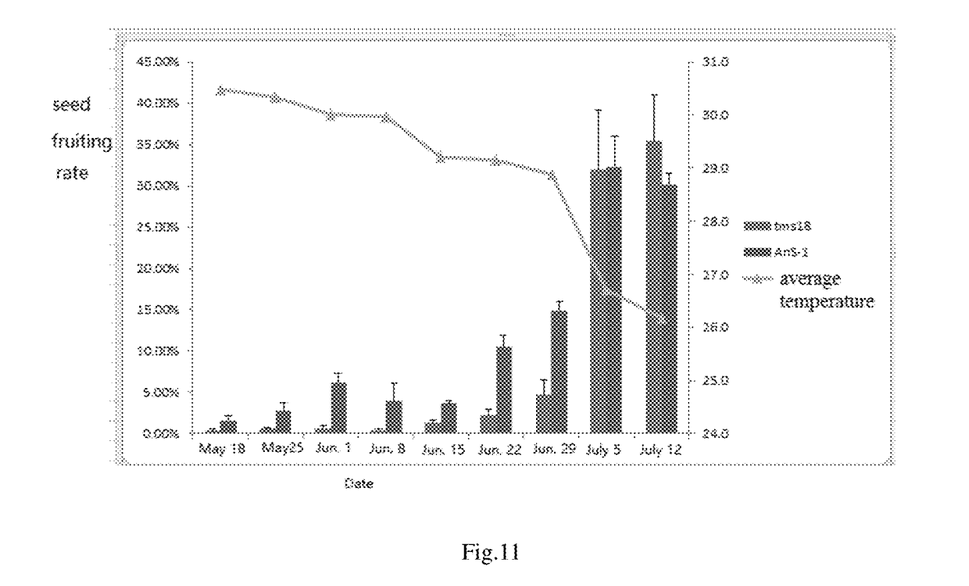
FIG. 11 shows the results of gene complementarity experiment.

Specifically, using wild-type plants as templates, the cDNA of light and temperature sensitive gene was amplified with specific primers, then constructed on Blunt through intermediate vector. The constructed results were amplified in large quantities, and then constructed on 1300-eGFP through BamHI and SalI digestion sites. The plasmid containing vector and eGFP was transformed into *Agrobacterium* EHA105, and then infected the heterozygous seeds of the corresponding mutants to obtain complementary transgenic plants. The complementary plants showed a normal fertile phenotype at high temperature, and the results are shown in FIG. 11.

The applicant identified the 11 transgenic lines (wherein 6 of them include tms18/tms18, i.e., the double strands of chromosomes both contain tms18). In high temperature environment (greater than 29° C.), these plants restored fertility and formed normal seeds compared with the non transgenic tms18/tms18 plant. The Figure in scanning electron microscope also showed that the pollen of transgenic plants returned to normal and there was no significant difference between wild-type and transgenic plants (FIG. 8B).

TMS18 gene encodes a protein with 587 amino acids and about 65 kDa. Structural analysis shows that TMS18 protein belongs to a member of glucose methanol choline (GMC) oxidoreductase family, which family widely exists in animals, plants and microorganisms, including glucose oxidase and pyranose oxidase (Wongnate and Chaiyen, 2013).

In the tms18 mutant plant, the microspore collapsed after the tetrad stage, indicating that the gene is closely related to the formation of pollen outer wall.

Molecular Mechanism of Tms18 Thermo Sensitive Genic Male Sterile Line

Through comparative observation of the plant containing wild-type gene and mutant gene, it is found that the temperature sensitive gene mutant of the invention is specifically expressed in anthers. The single base mutation of the gene caused the thinning of the second layer of pollen outer wall at high temperature, resulting in the thermo sensitive sterility phenotype.

Potential Application Value of Tms18 Thermo Sensitive Genic Male Sterile Line

At present, the sensitive period of fertility of most exist photosensitive male sterile lines, such as Photosensitive Genic Male Sterile Lines Nk58s and Ans-1, is before the meiotic tetrad period. However, there is no corresponding report on the materials for which sensitive period of fertility is in the later stage of meiosis, so the gene of the present invention has a good application prospect.

In the invention, the gene expression period of tms18 thermo sensitive genic male sterile line is mainly in the middle and late stage of anther, and the outer wall of pollen becomes thinner in the 9$^{th}$-11$^{th}$ stage of pollen development. This means that the temperature sensitive genic male sterile line may be affected by temperature, and the sensitive period may be after the meiosis period of pollen mother cell.

Since tms18 thermo sensitive genic male sterile lines are mainly affected by temperature in the later stage. Therefore, it can be used to solve the problem of easy recovery of low temperature tide in summer encountered in seed production. It can be used to hybridize with temperature sensitive genic male sterile lines and construct double mutants to prolong the period affected by temperature sensitivity, so as to try to solve some safety problems in seed production.

The amino acid sequence of the tms18 mutant of the invention is changed mainly from glycine to serine at the N-end of the protein, and other positions are not changed.

In conclusion, the inventor of the present application cloned and obtained the gene tms18 of glucose methanol choline (GMC) oxidoreductase family in rice, and found that the gene mutant showed the phenotype of photo thermo sensitive male sterility, which was not at the same site as the photo thermo sensitive genic male sterile line currently used in production. Cytological analysis showed that the integrity of the second layer of pollen outer wall of tms18 mutant had obvious thinning and fracture defects, which led to the rupture and abortion of pollen in the rapid expansion stage. However, the rupture of microspore outer wall recovered to a certain extent under low temperature treatment. Further analysis showed that tms18 protein was secreted by tapetum cells and specifically located on tapetum, anther and pollen surface. The inventor's research data show that tms18, as a new temperature sensitive genic male sterile line, its fertility sensitive period is mainly after meiosis of pollen mother cell, which is different from the light and temperature sensitive materials reported at present, and has significant application value.

The invention claimed is:

1. A rice seed, wherein the genome of said rice seed comprises the rice thermo-sensitive male sterile mutant tms18 gene consisting of the nucleotide sequence of SEQ ID No.1.

2. A method for cultivating rice, wherein the method includes introducing the rice thermo-sensitive male sterile mutant tms18 gene consisting of the nucleotide sequence of SEQ ID No.1 into rice seeds, and planting the rice seeds to obtain rice.

* * * * *

SEQUENCE LISTING

<160> NUMBER OF SEQ ID NOS: 1

<210> SEQ ID NO 1
<211> LENGTH: 2191
<212> TYPE: DNA
<213> ORGANISM: Oryza sativa

<400> SEQUENCE: 1

| | | | | | |
|---|---|---|---|---|---|
| atggcagcac | ttggccgcgc | gagctcgtcg | gcgccggtgc | ttgccgccgc | cgccgccgtg | 60 |
| ctcctctcgc | tctgcctcgc | cgcgctctcg | gaagagcaag | gtgcgtaaac | gttgcgttgt | 120 |
| atctttgcgt | tgatgcgtgt | tgcgtcgtcg | tcgtgttcat | ggcgtgcgat | ggcgttgtgc | 180 |
| agagcaactg | gagaacctgc | ggttcgtgcg | gcacgcgcag | gacgcgccgc | tggtgtcgag | 240 |
| ctacaactac | atcgtcatcg | gcagcggcac | ggcggggtgc | ccgctggcgg | cgacgctgtc | 300 |
| ggagcactcg | cgcgtgctgc | tgctggagcg | cggcggcctg | ccgtacgcca | acatgtcgag | 360 |
| cgagcagcac | ttcacggacg | cgctggccga | cacgtcgccg | gcgtcgccgg | cgcagcggtt | 420 |
| catctcggag | gacggcgtgg | tgaacgcccg | ggcgcgggtg | ctcggcggcg | ggagctgcct | 480 |
| caacgccggg | ttctacacgc | gggcgagcaa | cgagtacgtg | cgcgcctccg | ggtgggacgc | 540 |
| gcggctggtg | aactcgtcgt | accggtgggt | ggagcgctcg | ctggtgttcc | gccccgacgt | 600 |
| gccgccgtgg | caggcggcgc | tccgcgacgc | gctgctcgag | gtcggcgtca | cgcccgacaa | 660 |
| cggcttcacc | ttcgaccacg | tcaccggcac | caagatcggc | ggcaccatct | tcgacaactc | 720 |
| cggccagcgc | cacaccgccg | ccgacttcct | ccgccacgcc | cgccccgcg | gcctcaccgt | 780 |
| cctcctctac | gccaccgtct | cccgtatcct | cttcaaaagc | caaggtacac | agctacgatg | 840 |
| aaaatggaaa | atgtgctgtg | cgccgaagaa | gcttgacctc | acgacggcga | gcttttgcca | 900 |
| tggcgtgcag | acggggtgcc | gtacccggtg | gcgtacgggg | tggtgttctc | ggacccgctg | 960 |
| ggggtgcagc | accgggtgta | cctccgcgac | ggcgacaaga | acgaggtgat | cgtgtcggcg | 1020 |
| gggacgctgg | ggagcccgca | gctgctgatg | ctgagcggcg | tcgggccgca | ggcgcacctg | 1080 |
| gaggcgcacg | gcatcgaggt | gatcgtggac | caacccatgg | tcgggcaggg | cgtcgccgac | 1140 |
| aacccgatga | actcggtgtt | catcccgtcg | ccggtgccgg | tggagctctc | cctggtgcag | 1200 |
| gtcgtcggca | tcacccgctc | cggcagcttc | atcgaggggg | tgagcgggtc | ggagttcggc | 1260 |

```
atgccggtgt cggacggcgc gctccggtgg gcgcgcagct tcgggatgct gtcgccgcag    1320
acggggcagc tcggcacgct gccgccgaag cagaggacgc cggaggcgct gcagcgggcg    1380
gcggaggcga tgatgcggct ggacaggagg gcgttccggg gaggcttcat cctggagaag    1440
atcctcgggc cggtgtcctc cggccacgtc gagctgcgaa ccaccgaccc gagggcgaac    1500
ccgtcggtga cgttcaacta cttccgcgag gcagaggatc tggagcggtg cgtccatggc    1560
atcgagacga tcgagcgggt gatccagtcg cgggccttct ccaacttcac ctacgccaac    1620
gcctccgtcg agtccatctt caccgattcc gccaacttcc ccgtcaacct gctgccgcgc    1680
catgtcaacg actcgcgctc gccggagcag tactgcatgg acaccgtcat gaccatctgg    1740
cactaccacg gcggctgcca tgtcggcgcc gtcgtcgacg acgattaccg ggtgttcggg    1800
gtgcaggggc tcagggtgat cgacagctcc accttcaagt actcccccgg caccaaccct    1860
caggccaccg tcatgatgct cggcaggtaa ctggcatcat tttagctcat gaaagtgcat    1920
tgccatgagt aacaacacac taacagtata gttttcaata tggacactgg gcaggtatat    1980
gggtgtgaag attcagtccg agagatggaa gaaatgatga acaaaagata atttcgtttc    2040
aggagcaaaa aaatgcatgt aattcaagga aaagaaaatg ttcaactgtc tttagagttt    2100
agagtagatt ttatttgcac ccacttaatt tttactcttc tctagacata ggttcagtat    2160
ctgcttgttg attatgtaac cttgaagaag c                                  2191
```